US009310301B2

(12) United States Patent
Sandell et al.

(10) Patent No.: US 9,310,301 B2
(45) Date of Patent: Apr. 12, 2016

(54) LENS ASSEMBLY FOR BIOLOGICAL TESTING

(75) Inventors: Donald Sandell, San Jose, CA (US); Eugene Young, Marietta, GA (US); Steven Boege, San Mateo, CA (US)

(73) Assignee: APPLIED BIOSYSTEMS, LLC, Carlsbad, CA (US)

( * ) Notice: Subject to any disclaimer, the term of this patent is extended or adjusted under 35 U.S.C. 154(b) by 0 days.

(21) Appl. No.: 13/468,964

(22) Filed: May 10, 2012

(65) Prior Publication Data

US 2013/0052723 A1    Feb. 28, 2013

Related U.S. Application Data

(60) Continuation of application No. 11/225,934, filed on Sep. 13, 2005, now abandoned, which is a division of application No. 10/146,066, filed on May 16, 2002, now Pat. No. 6,982,166.

(51) Int. Cl.
| | |
|---|---|
| *B01L 7/00* | (2006.01) |
| *G01N 1/00* | (2006.01) |
| *G01N 21/64* | (2006.01) |
| *G01N 21/25* | (2006.01) |
| *G02B 3/00* | (2006.01) |
| *G02B 3/08* | (2006.01) |

(52) U.S. Cl.
CPC .............. *G01N 21/6452* (2013.01); *B01L 7/52* (2013.01); *G01N 21/253* (2013.01); *B01L 2300/046* (2013.01); *B01L 2300/0654* (2013.01); *B01L 2300/0829* (2013.01); *G02B 3/0056* (2013.01); *G02B 3/08* (2013.01)

(58) Field of Classification Search
CPC ... B01L 7/52; B01L 2300/046; G01N 21/253; G01N 21/6452
See application file for complete search history.

(56) References Cited

U.S. PATENT DOCUMENTS

| | | | |
|---|---|---|---|
| 5,096,807 A | 3/1992 | Leaback | |
| 5,234,665 A | 8/1993 | Ohta et al. | |
| 5,315,375 A | 5/1994 | Allen | |
| 5,682,232 A | 10/1997 | Tajima et al. | |
| 5,734,496 A | 3/1998 | Beach | |
| 5,774,214 A | 6/1998 | Prettyjohns et al. | |
| 5,780,857 A | 7/1998 | Harju et al. | |

(Continued)

FOREIGN PATENT DOCUMENTS

| | | |
|---|---|---|
| DE | 19748211 | 5/1999 |
| DE | 20321717 | 4/2009 |

(Continued)

OTHER PUBLICATIONS

"Extended European Search Report for EP App No. 09152555", Mar. 27, 2009.

(Continued)

*Primary Examiner* — Nathan Bowers

(57) ABSTRACT

The invention relates to an optical detection system for a thermal cycling device including at least one light source, a light detection device for detecting light received from a plurality of biological samples, and a lens having first and second surfaces formed on the lens, the second surface substantially opposed to the first surface. The first surface may be configured to collimate light and the second surface may be configured to direct light into each of the plurality of biological samples.

17 Claims, 5 Drawing Sheets

(56) References Cited

U.S. PATENT DOCUMENTS

| | | | |
|---|---|---|---|
| 5,892,577 A | 4/1999 | Gordon | |
| 5,928,907 A * | 7/1999 | Woudenberg et al. | 435/91.2 |
| 5,961,926 A | 10/1999 | Kolb et al. | |
| 5,993,746 A | 11/1999 | Priha et al. | |
| 6,008,892 A | 12/1999 | Kain et al. | |
| 6,015,674 A | 1/2000 | Woudenberg et al. | |
| 6,024,920 A | 2/2000 | Cunanan | |
| 6,027,695 A | 2/2000 | Oldenburg et al. | |
| 6,033,605 A | 3/2000 | Szlosek | |
| 6,130,745 A | 10/2000 | Manian | |
| 6,232,114 B1 | 5/2001 | Coassin et al. | |
| 6,238,911 B1 | 5/2001 | Kasahara | |
| 6,246,525 B1 * | 6/2001 | Ikami | 359/619 |
| 6,256,088 B1 | 7/2001 | Gordon | |
| 6,258,326 B1 | 7/2001 | Modlin | |
| 6,262,846 B1 | 7/2001 | Nakai | |
| 6,271,972 B1 | 8/2001 | Kedar et al. | |
| 6,272,939 B1 | 8/2001 | Frye et al. | |
| 6,278,560 B1 * | 8/2001 | Hendriks | 359/738 |
| 6,280,960 B1 | 8/2001 | Carr | |
| 6,304,378 B1 | 10/2001 | Clausen | |
| 6,330,017 B1 * | 12/2001 | Suzuki | 347/238 |
| 6,366,405 B2 | 4/2002 | Abe | |
| 6,381,072 B1 | 4/2002 | Burger | |
| 6,388,788 B1 | 5/2002 | Harris | |
| 6,399,952 B1 | 6/2002 | Maher et al. | |
| 6,437,345 B1 | 8/2002 | Bruno-Raimondi | |
| 6,473,239 B1 * | 10/2002 | Volcker et al. | 359/624 |
| 6,514,750 B2 | 2/2003 | Bordenkircher et al. | |
| 6,563,581 B1 | 5/2003 | Oldham et al. | |
| 6,750,457 B2 | 6/2004 | Heffelfinger et al. | |
| 6,818,437 B1 | 11/2004 | Gambini et al. | |
| 6,942,836 B2 | 9/2005 | Freudenthal et al. | |
| 7,407,798 B2 | 8/2008 | Oldham et al. | |
| 2002/0168665 A1 | 11/2002 | Okawa | |
| 2003/0044967 A1 | 3/2003 | Heffelfinger et al. | |

FOREIGN PATENT DOCUMENTS

| | | |
|---|---|---|
| EP | 0395156 | 10/1990 |
| EP | 0545284 | 6/1993 |
| EP | 0814300 | 12/1997 |
| EP | 2053429 | 4/2009 |
| GB | 2187567 | 9/1987 |
| JP | 02210310 | 8/1990 |
| JP | 02280707 | 11/1990 |
| JP | 11-500232 | 1/1999 |
| JP | 11202105 | 7/1999 |
| JP | 2001166254 | 6/2001 |
| JP | 2002-507762 | 3/2002 |
| JP | 2002527743 | 8/2002 |
| JP | 2009-216711 | 9/2009 |
| JP | 2009222506 | 10/2009 |
| WO | WO-95/30139 | 11/1995 |
| WO | WO-97/36681 | 10/1997 |
| WO | WO-98/10314 | 3/1998 |
| WO | WO-98/57151 | 12/1998 |
| WO | WO-99/60381 | 11/1999 |
| WO | WO-00/22417 | 4/2000 |
| WO | WO 00/22417 * | 4/2000 |
| WO | WO-0025922 | 5/2000 |
| WO | WO-00/58715 | 10/2000 |
| WO | WO-00/65325 | 11/2000 |
| WO | WO-01/28684 | 4/2001 |
| WO | WO-01/35079 | 5/2001 |
| WO | WO-01/35097 | 5/2001 |
| WO | WO-03/098282 | 11/2003 |

OTHER PUBLICATIONS

Canning, et al., "Silica-Based Fibre Fresnel Lens", *Optics Communications*, vol. 199, Issues 5-6, Dec. 2001, 375-381.

Cohn, Robert et al., "Fully Complex Diffractive Optics by Means of Patterned Diffuser Arrays: encoding Concept and Implications for Fabrication", *J. Opt. Soc. Am. A*, vol. 14 No. 5, May 1997, 1110-1123.

EP 09152555.0, "Annex to the European Search Report mailed Mar. 20, 2009", 1 pg.

EP 09152555.0, "European Search Report mailed Mar. 20, 2009", 1 pg.

EP 10183609.6, "Extended European Search Report mailed Feb. 23, 2011", 4 pgs.

Hasman, et al., "Three-Dimensional Optical Metrology With Color-Coded Extended Depth of Focus", *Optics Letters*, vol. 24, No. 7, Apr. 1, 1999, 439-441.

PCT/US03/15586, "International Search Report dated Aug. 18, 2003", Aug. 18, 2003, 3 pgs.

Yasubiro, Tanaka et al., "Diffractive-Refractive Achromatic Lens for Optical Disk System by Glass Molding", *Optical Review*; vol. 5, No. 6., 1998, 334-339.

* cited by examiner

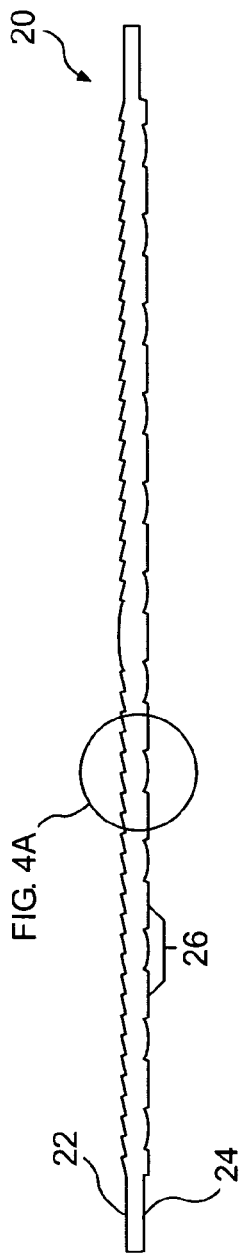
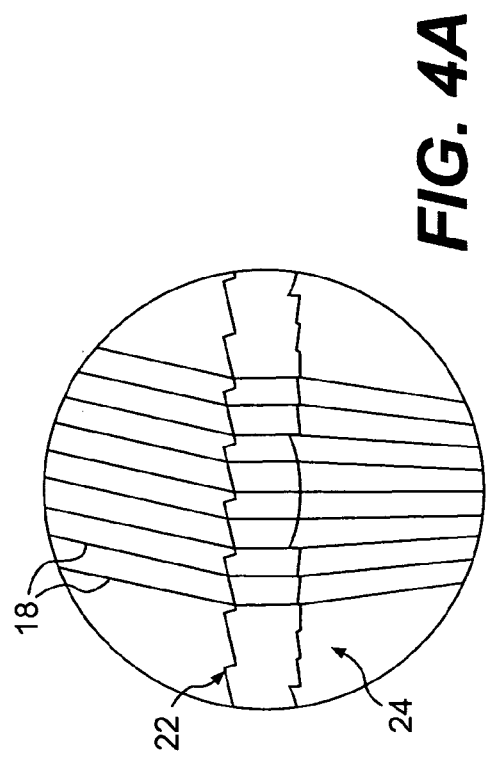

LENS ASSEMBLY FOR BIOLOGICAL TESTING

CROSS-REFERENCE TO RELATED APPLICATION

This application is a continuation application of U.S. patent application Ser. No. 11/225,934 filed on Sep. 13, 2005, which is a divisional of U.S. patent application Ser. No. 10/146,066 filed May 16, 2002, now U.S. Pat. No. 6,982,166, which disclosures are herein incorporated by reference in their entirety as if fully set forth herein.

BACKGROUND OF THE INVENTION

1. Field of the Invention

The present invention relates to an optical system for focusing light onto one or more samples in a system for biological testing. In one aspect, the invention relates to a lens assembly having the functions of collimating and focusing light onto one or more samples integrated into the lens assembly.

2. Description of the Related Art

Biological testing has become an important tool in detecting and monitoring diseases. In the biological testing field, thermal cycling is used to amplify nucleic acids by, for example, performing PCR and other reactions. PCR in particular has become a valuable research tool with applications such as cloning, analysis of genetic expression, DNA sequencing, and drug discovery.

Recent developments in the field have spurred growth in the number of tests that are performed. One method for increasing the throughput of such biological testing is to provide real-time detection capability during thermal cycling. Real-time detection increases the efficiency of the biological testing because the characteristics of the samples can be detected while the sample well tray remains positioned in the thermal cycling device.

In a real-time detection system testing may be performed on multiple samples during a cycle of the testing device. With this type of system, light may be emitted from a light source to be reflected off of the biological sample(s) and ultimately may be detected or collected by a light detecting device such as a camera or CCD, for example. To assist in the focusing the light into and directed the light out of the samples toward detecting device, one or more lenses may be provided.

One of the drawbacks of conventional devices utilizing lens assemblies in conjunction with multiple sample testing devices is the complexity of the lens(es). It may often be desirable to have a lens for collimating light so that it may be properly aligned with a row or column of sample wells in a sample well tray. To further enhance the testing process, an additional lens assembly may be provided for focusing light more precisely within each of the sample wells. These focusing lens assemblies often may comprise a plurality of non-integral components.

SUMMARY OF THE INVENTION

In accordance with the invention, an optical detection system for a thermal cycling device is disclosed including at least one light source, a light detection device for detecting light received from a plurality of biological samples, and a lens having first and second surfaces formed on the lens, the second surface substantially opposed to the first surface. The first surface may be configured to collimate light and the second surface may be configured to direct light into each of the plurality of biological samples.

According to another aspect, the second surface may comprise a matrix of lenses formed into the second surface and the matrix may comprise a plurality of focusing lens portions.

According to yet another aspect, a plurality of focusing lens portions may correspond to a plurality of biological samples.

In another aspect, the matrix may comprise 4, 8, 12, 24, 48, 96, 384, or 1,536 focusing lens portions.

In yet another aspect, the system may further include a sample block assembly configured to receive a sample well tray.

In yet a further aspect, the sample block assembly may be configured to receive the lens.

In another aspect, the sample block assembly may include a heated cover configured to receive the lens.

In yet another aspect, the lens may be mounted to the sample block assembly with at least one fastening device.

According to another aspect, the fastening device may comprise one of a clip-fastening device, a clamp-fastening device, and a screw-fastening device.

According to yet another aspect, the heated cover and the sample block assembly may be configured to heat the biological samples to a temperature of approximately 80° C. or greater and the lens may comprise a material configured to operate up to a temperature of at least 80° C.

According to another aspect, the lens material may comprise a non-fluorescing clear polycarbonate.

In another aspect, the sample block assembly may be configured to heat the sample tray assembly to a temperature of approximately 60° C. and the lens may comprise a material configured to operate up to a temperature of at least 60° C.

In yet another aspect, the lens material may be chosen from acrylics, styrenes, polyethylenes, polycarbonates, and polypropylenes.

According to another aspect, the first lens surface and the second lens surface may be integrally formed by at least one of injection molding and compression molding.

According to yet another aspect, a plurality of focusing lens portions may be configured to direct light of an approximately equal intensity into a plurality of biological samples.

According to a further aspect, one or more of the plurality of focusing lens portions may be configured to allow differing light intensity to pass through than at least one other of the plurality of focusing lens portions.

In another aspect, the one or more of the plurality of focusing lens portions comprises a smaller focusing lens portion than at least one other of the plurality of focusing lens portions.

In yet another aspect, part of the one or more of the plurality of focusing lens portions may be masked to differ the intensity of light passing through the one or more of the plurality of focusing lens portions.

In another aspect, the first lens surface may comprise a fresnel lens.

In yet another aspect, the at least one light source may provide light of a non-uniform intensity across the first surface, and the second surface may be configured to provide light at approximately uniform intensity to each of the plurality of biological samples.

According to another aspect, biological samples may have corresponding focusing lens segments.

In another aspect, lens for an optical detection system of a thermal cycling device is disclosed. The lens may include a collimating surface and a matrix surface substantially opposed to the first lens surface and the matrix surface may include a plurality of focusing lens segments. The collimating surface may be configured to collimate light from a light source, and the plurality of focusing lens segments may be configured to direct light into a plurality of biological samples.

In yet another aspect, the collimating surface and the matrix surface may be integrally formed by at least one of injection molding and compression molding.

According to another aspect, each of the plurality of focusing lens segments may be configured to direct light at an approximately equal intensity.

According to yet another aspect, one or more of the plurality of focusing lens segments may be configured to allow differing intensity of light to pass through than at least one other of the plurality of focusing lens segments.

In another aspect, the one or more of the plurality of focusing lens segments may comprise a smaller focusing lens segment than at least one other of the plurality of focusing lens segments.

In yet another aspect, a portion of the one or more focusing lens segments may be masked to differ the intensity of light passing through the one or more of the focusing lens segments.

In a further aspect, the lens may comprise 4, 8, 12, 24, 48, 96, 384, or 1,536 focusing lens segments.

According to another aspect, the lens may comprise a one-piece lens.

In another aspect, an optical detection system for a thermal cycling device is disclosed, the system may include at least one light source, a light detection device for detecting light received from a plurality of biological samples, a lens body having a first surface formed into the lens body and a second surface formed into the other side of the body, and a sample block assembly configured to receive a sample well tray. The sample well tray may be configured to contain the plurality of biological samples and the sample block assembly may include a heated cover configured to receive the lens. Further, the first surface may be configured to collimate light and the second surface may comprise a lens matrix having a plurality of focusing lens portions configured to direct light into each of the plurality of biological samples.

According to yet another aspect, a method of testing a plurality of biological samples is disclosed. The method may include providing light from at least one light source, providing a light detection device for detecting light received from the plurality of biological samples, providing a lens having a collimating lens portion formed on a first surface of the lens and a matrix of focusing lens portions formed on a second surface of the lens with the first surface substantially opposed to the second surface. Light may pass through the collimating and focusing lens portions into the plurality of biological samples and may be detected by the detection device.

Other aspects still will become apparent from the detailed description that follows. It should be understood that the invention, in its broadest sense, could be practiced without accomplishing one or more of the aspects described herein.

BRIEF DESCRIPTION OF THE DRAWINGS

The accompanying drawings, which are incorporated in and constitute a part of this specification, illustrate at least one exemplary embodiment of the invention. In the drawings.

FIG. 4 is a section view of the single-piece lens of FIG. 2;

FIG. 4a is a close-up view of the circled portion of FIG. 4; and

DESCRIPTION OF THE EMBODIMENTS

Figure 1:
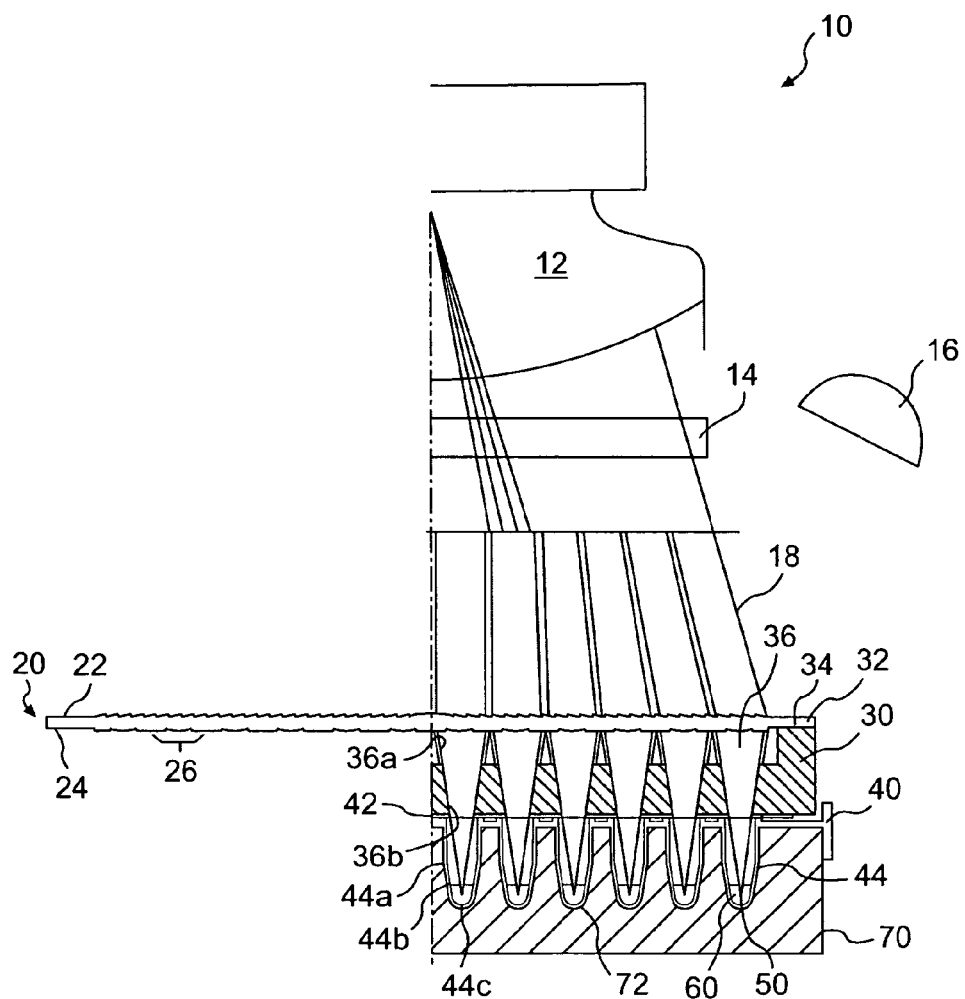
FIG. 1 is a partial section view of a biological testing device according to an exemplary embodiment of the invention.

Reference will now be made in detail to exemplary embodiments of the invention, examples of which are illustrated in the accompanying drawings. Wherever possible, the same reference numbers are used in the drawings and the description to refer to the same or like parts, and the same reference numbers with alphabetical suffixes or numerical prefixes are used to refer to similar parts.

In accordance with certain embodiments, a biological testing device is provided. In one aspect, the biological testing device may perform nucleic acid amplification. In certain embodiments, the biological testing device includes a light source, a light detection device, and a lens. In various embodiments, the biological testing device may also include a sample block, a heated cover, a sample well tray, a seal for covering openings of the sample wells in the sample well tray, a light refractor, a light reflector, or a filter, among other components.

In FIG. 1, a generally schematic view is shown that is representative of a biological testing device 10 according to an embodiment of the invention. Testing device 10 may be any type of device configured to perform nucleic acid amplification. One common method of performing nucleic acid amplification of biological samples is polymerase chain reaction (PCR). Various PCR methods are known in the art, as described in, for example, U.S. Pat. Nos. 5,928,907 and 6,015,674 to Woudenberg et al., the complete disclosures of which are hereby incorporated by reference for any purpose. Other methods of nucleic acid amplification include, for example, ligase chain reaction, oligonucleotide ligations assay, and hybridization assay. These and other methods are described in greater detail in U.S. Pat. Nos. 5,928,907 and 6,015,674.

In one embodiment, the thermal cycling device performs real-time detection of the nucleic acid amplification of the samples during thermal cycling. Real-time detection systems are known in the art, as also described in greater detail in, for example, U.S. Pat. Nos. 5,928,907 and 6,015,674 to Woudenberg et al., incorporated herein above. During real-time detection, various characteristics of the samples are detected during the thermal cycling in a manner known in the art. Real-time detection permits more accurate and efficient detection and monitoring of the samples during the nucleic acid amplification.

In accordance with various embodiments, the testing device may include a light or radiation source. As embodied herein and shown in FIG. 1, the testing device includes a light source 16 for directing light onto a plurality of biological samples. The biological samples may be positioned in any type of known sample-receiving member. In the embodiment shown in FIG. 1, the samples 60 are located in sample wells 44 of sample well tray 40. Light source 16 may be any conventional type of light source suitable for biological testing, such as a quartz bulb, a laser, (e.g. an argon ion laser), or an LED, for example. Light emitted from light source 16 may be aimed directly toward sample well tray 40, or light source 16 could be aimed at a beam splitter (not shown) that then may redirect at least a portion of the light toward sample well tray 40.

In accordance with various embodiments, biological testing device 10 includes an optical detection system. As embodied herein and shown in FIG. 1, an optical detection device 12 is positioned above the sample well tray 40. The optical detection system 12 is configured to detect and monitor the characteristics of the samples in the sample well tray 40 during the testing. Suitable structures and methods for the optical detection device 12 are well known in the art. The optical detection device may use any known structure or method. In one example, the optical detection device could include a CCD camera, in a manner known in the art. Likewise, the optical detection device may include any other type suitable for use with the thermal cycling device of the present invention.

In certain embodiments, a filter 14 may be provided for filtering the light reflected from the sample and allowing only a predetermined range of light waves to enter the optical detection device 12. Other elements known to be included in detecting devices may be included in testing device 10, such as a prism, a mirror, or a spectrograph, among others.

In accordance with various embodiments, a seal may be provided for the sample well tray. In one embodiment shown in FIG. 1, sample well tray 40 is covered by a film 42 for sealing the various sample wells 44 and for aiding in minimizing contamination of biological samples 60. Film 42 may be provided with an adhesive on the side facing sample well tray 40 to secure it in place. The film may be made out of any known material suitable for use with a sample well tray.

In accordance with various embodiments, the biological testing device can include a heated cover. In the embodiment shown in FIG. 1, a cover 30 is located above film 42. As shown in FIG. 1, cover 30 includes a lip 32 around its perimeter. Lip 32 may be continuous or it may also be discontinuous. Lip 32 is raised above surface 34 onto which a lens 20 may be placed. In combination, lip 32 and surface 34 may serve to locate and hold lens 20 in a desired position in relation to cover 30. Cover 30 also includes a plurality of openings 36, with each opening being positioned over one of sample wells 44 to allow light to pass through cover 30 and into biological samples 60 in the sample wells 44. As depicted in FIG. 1, openings 36 taper from an upper edge 36a to a lower edge 36b. In certain embodiments, cover 30 may be heated to augment heating of biological samples 60 provided by a sample block 70. Acting as a heated cover, cover 30 may also serve a function to reduce condensation within the system.

In the embodiment shown, cover 30 rests on film 42, which in turn rests or is adhered to sample well tray 40. Sample well tray 40 may be any member utilized in biological testing to hold one or more samples. In the embodiment shown in FIG. 1, sample well tray 40 includes a plurality of sample wells 44. Sample wells 44 comprise an upper portion 44a that has a substantially cylindrical shape and a tapered lower portion 44b that ends in a rounded bottom portion 44c.

Biological testing device 10 may be configured for use with any type of sample well tray, including, for example, 96-well sample well trays, 384-well sample trays, and microcard sample trays. The size and shape of these sample well trays are well known in the art. Examples of 96-well sample well trays suitable for use in the present invention are described in WO 00/25922 to Moring et al., the complete disclosure of which is hereby incorporated by reference for any purpose. Examples of sample well trays of the microcard type suitable for use in the present invention are described in WO 01/28684 to Frye et al., the complete disclosure of which is hereby incorporated by reference for any purpose, WO97/36681 to Woudenberg et al., the complete disclosure of which is hereby incorporated by reference for any purpose, U.S. application Ser. No. 09/897,500, filed Jul. 3, 2001, assigned to the assignee of the present invention, the complete disclosure of which is hereby incorporated by reference for any purpose, and U.S. application Ser. No. 09/977,225, filed Oct. 16, 2001, assigned to the assignee of the present application, the complete disclosure of which is hereby incorporated by reference for any purpose. Sample well trays having any number of sample wells and sample well sizes may also be used with the thermal cycling device of the present invention. In the example shown in the figures, the volume of the sample wells may vary anywhere from about 0.01 µl to thousands of microliters (µl), with a volume between 10 to 500 µl being typical.

In the embodiment shown in FIG. 1, sample well tray 40 includes a plurality of sample wells 44 for holding biological samples 60. In the example shown in FIG. 1, each sample well comprises an upper cylindrical portion 44a and a tapered portion 44b that ends in a rounded bottom portion 44c. It is well understood that the sample wells may have any known size, shape, or configuration.

In accordance with various embodiments, the testing device may include a sample block. As embodied herein and shown in FIG. 1, sample well tray 40 is configured to mount onto sample block 70. Sample block 70 may be any sample block known in the art that is used to receive a sample well tray and provide heating and/or cooling of biological samples 60. Sample block 70 may be machined or cast of a material suitable for conducting heat to sample tray 40 and includes a plurality sample well openings 72 equal in number to a number of sample wells 44 of sample tray 40.

As mentioned above, lens 20 may rest on, or be otherwise adjacent to, cover 30 and may perform the function of both focusing and collimating light emitted from and/or directed to samples 60. Lens 20 comprises at least two surfaces: a first surface 22 facing detection device 12 and a second surface 24 facing sample well tray 40. As used herein, "surface" is intended to broadly define a generally planar external portion of the lens that may include a plurality of sub-surfaces formed into the surface with the various sub-surfaces providing the desired overall lens characteristics. First surface 22 comprises a Fresnel lens for collimating light and second surface 24 includes a matrix 25 having a plurality of focusing lens portions or segments 26 equal to the number of sample wells 44. Each focusing lens portion or segment 26 is defined as the portion of surface 24 configured to focus light into an individual sample 60. Lens 20 will be described in greater detail below.

Figure 2:
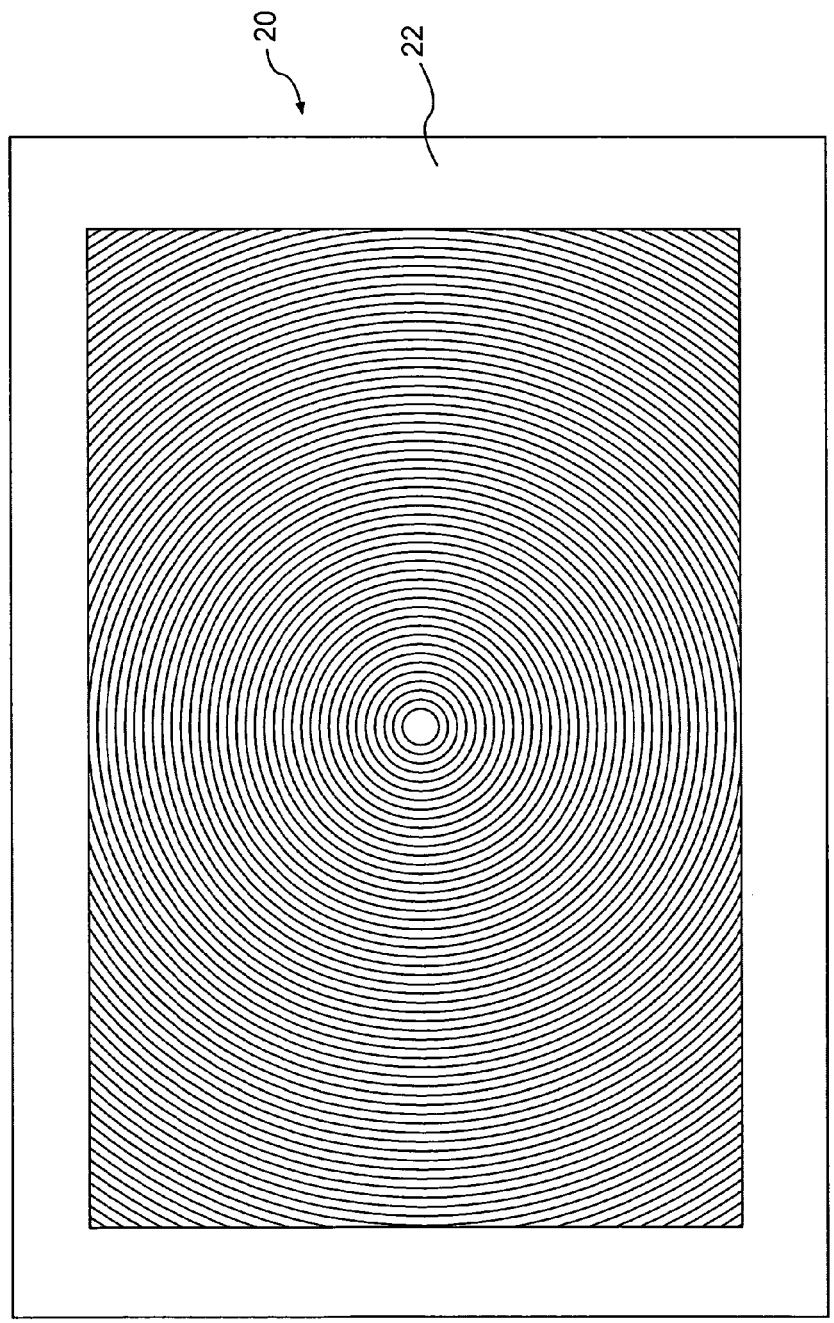
FIG. 2 is a plan view of a first side of a single-piece lens depicted in FIG. 1.

As can be seen in FIG. 1, light is emitted from light source 16 and contacts first surface 22 of lens 20. FIG. 2 shows the configuration of first surface 22. This configuration may be a Fresnel lens of the type manufactured by the Fresnel Technologies of Fort Worth Tex. There are at least two basic types of Fresnel lenses. The first has a constant pitch with increased depth toward the outer edges and the second has a uniform depth. Either configuration could be used, but the uniform depth Fresnel lens is depicted in the embodiment shown in FIGS. 1-4.

Figure 3:
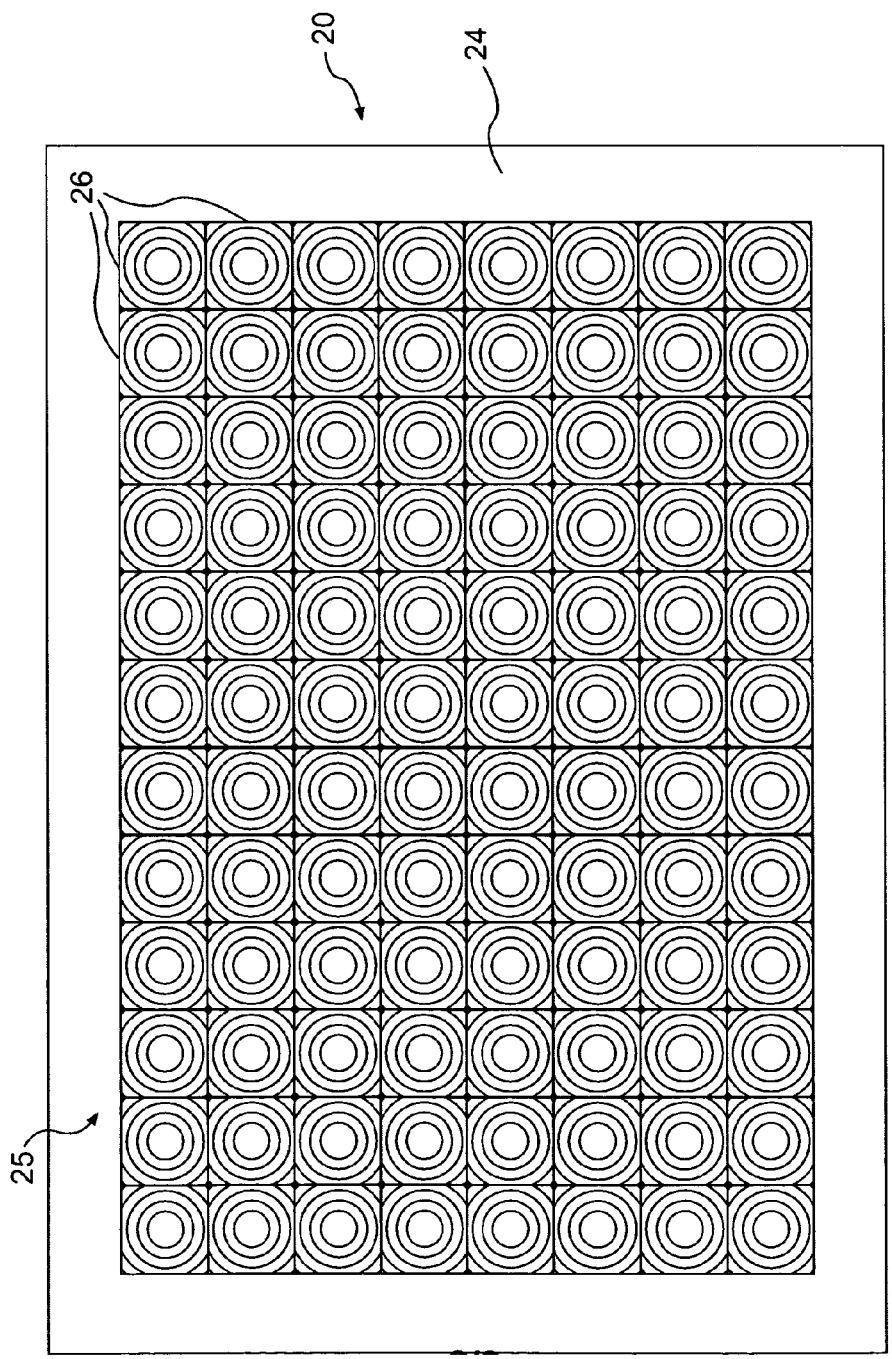
FIG. 3 is a plan view of a second side of the single-piece lens of FIG. 2.

In the embodiment shown, first surface 22 is used to collimate light beams 18 so that the light is directed toward each of the rows or columns of sample wells 44 of sample well tray 40. Light beams 18 then pass through to a second surface 24 of lens 20 which has formed on its surface a matrix 25 of focusing lenses (or focusing lens segments) 26 as shown in FIG. 3 for focusing light into each of biological samples 60 located in sample wells 44. Radiation, for example fluorescent radiation, from the samples 60 may pass through lens 20 in a reverse direction. Lens 20 serves to collect the reflected light and direct it toward detecting device 12.

As seen in FIG. 4A in a close-up view of light passing through one of the focusing lens segments 26, light beams 18 pass through first side of lens 22 and are collimated. As beams 18 pass through the second surface 24, they are focused toward the desired sample location. As depicted, each lens segment 26 comprises an individual Fresnel lens of concentric rings to accomplish the focusing. Although a Fresnel focusing lens is shown, other focusing lenses that may be formed into the second surface of the lens may be suitable as well.

In the embodiment shown in FIGS. 1-4, lens 20 integrates both the collimating function of side 22 and the focusing function of side 24 into the lens. First, as can be seen in FIG. 4, by forming the focusing lens segments 26 into the second surface 24 of lens 20, focusing lens segment 26 may occupy a substantial portion of the area over its associated sample well 44. This expanded lens allows for a maximum amount of light to pass into each of the samples 60. In addition, focusing lens segments 26, being formed into the second surface 24, are fixed in relation to each other, thus minimizing the potential for movement between respective focusing lens segments.

Also, by integrating Fresnel lens side 22 and focusing lens side 24 into a opposing surfaces of lens 20, the potential for misalignment may be reduced or even eliminated between the collimating and focusing functions. Because Fresnel lens side 22 and focusing lens side 24 of lens 20 are fixed in relation to each other, a correct alignment with respect to each other may be desirably maintained.

As described herein and shown in FIG. 1, heated cover 30 may also provide a mounting surface 34 for lens 20 that may assist in maintaining a proper alignment between lens 20 and sample well tray 40. Further enhancing this alignment, lens 20 can optionally be fastened to heated cover 30 by any fastening means known in the art (e.g., a mechanical device such as clips, clamps, screws, adhesives, etc.) so as to further reduce movement and alignment problems between lens 20 and heated cover 30.

In another aspect, lens 20 may be configured so that one or more of lens segments 26 may provide light of a different intensity as compared to another of lens segments 26. As mentioned above, light source 16 may be a quartz light. Light sources such as this often emit light of focused intensity that is concentrated at a central area of lens 20. As one moves toward the periphery of the lens assembly, the light emitted by light source 16 may be diminished. To compensate for this, one or more of focusing lens segments 26 may be configured in such a way as to substantially equalize the intensity of the light that is focused into each of the samples 60.

In certain embodiments, for example, the focusing lens segments 26 located near the center of lens 20 could be molded in a fashion whereby the optics of the individual focusing lens segments could be varied so that they allow less light to pass through than focusing lens segments located at a periphery of lens 20. Any or all of focusing lens segments 26 could be altered in a similar fashion to correspond to varying intensities of light directed onto the grid of lens 20. This could also be accomplished, for example, by masking a portion of selected focusing lens segments to reduce the amount of light that passes through them. The term "mask(ing)" as used herein is intended to mean reducing or completely inhibiting the light transmission capability of at least a portion of each of the focusing lens(es). This could be accomplished by applying a coating, for example paint, that would occlude at least a portion of the focusing lens segment. Masking could also include applying an adhesive material such as tape to a portion of the focusing lens segment for reducing the amount of light that passes through the lens. This masking could be done in various amounts throughout the lens matrix to achieve the desired intensity of light into each of the samples 60.

Lens 20 may be made by any suitable method. For example, it is contemplated that lens 20 could be manufactured by injection or compression molding. Lens 20 could be made of a non-fluorescing clear polycarbonate, for example. Testing devices using a heated cover, such as heated cover 30, often operate at temperatures approaching or even exceeding 80° C. For such high-temperature devices, a material such as Lexan is suitable for lens 20. Devices operating at lower temperatures, for example at or near 60° C., may include a lens made of any number of materials such as acrylics, styrenes, polyethylenes, polycarbonates, polypropylenes, or any other transparent plastic that may be suitable. Other materials may also be contemplated that would provide the same or similar characteristics as the ones included herein.

Although lens 20 is shown in a 12×8 grid configuration comprising 96 focusing lens segments, it is to be understood that this lens configuration could be modified into substantially any configuration to correspond with various sample well tray configurations or shapes. For example, lens 20 could have 4, 8, 12, 24, 384, or 1536 focusing lens segments. Lens 20 could also be formed in various shapes other than a rectangle so as to conform to a shape of a sample well tray.

FIGS. 1-4 show the lens 20 in combination with a heated cover 30 and sample well tray 40 with a plurality of sample wells 44. In certain embodiments, lens 20 can be used with other sample testing devices that may or may not have a heated cover. For example, FIG. 5 shows the lens 20 in use with a sample testing device that does not have a heated cover.

Figure 5:
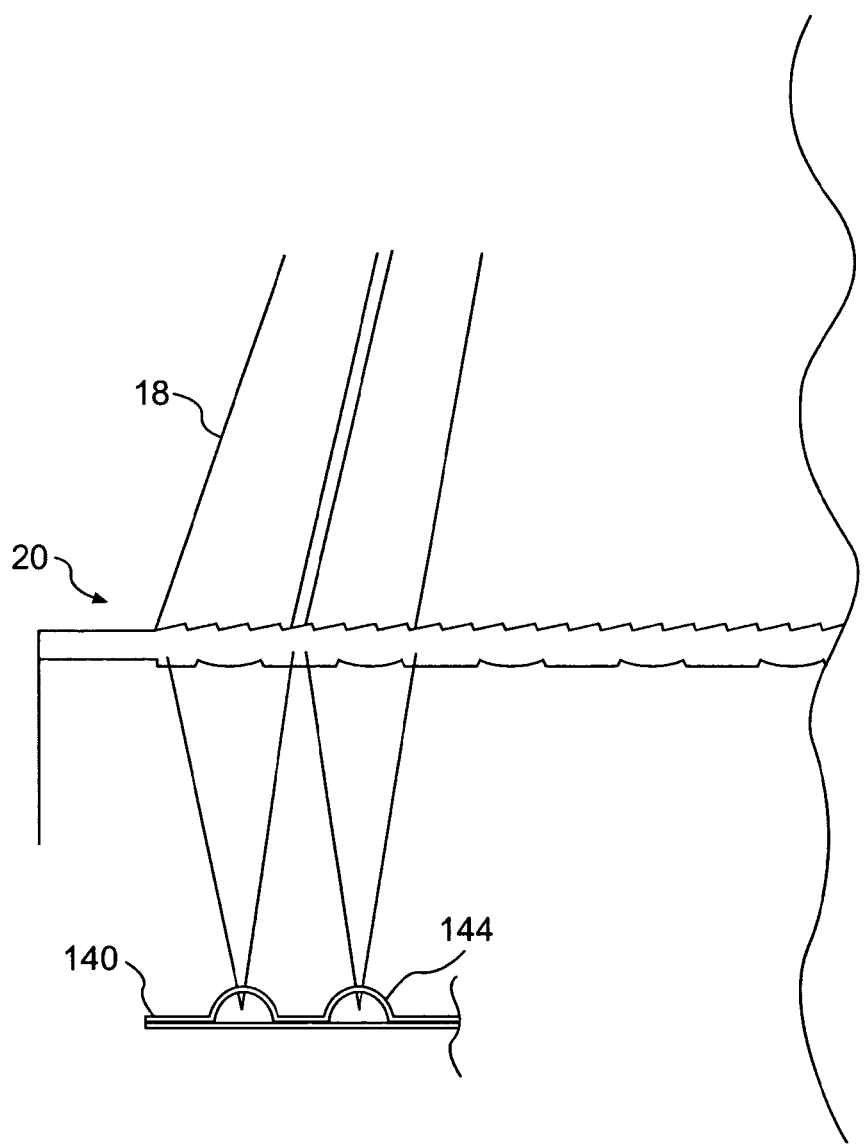
FIG. 5 is a partial section of the lens of FIG. 1 in combination with a microcard sample tray.

In FIG. 5, lens 20 is used in combination with a microcard sample tray 140. Microcard sample trays are known in the art as discussed above. In the embodiment shown in FIG. 5, microcard sample tray 140 includes a plurality of sample wells or chambers 144 configured to contain a sample for testing. Chambers 144 may align with a matrix of lenses in a fashion similar to the sample well tray 40 of FIG. 1. Microcard sample tray 140 can have any of the various configurations, sizes and shapes known in the art. In the embodiment shown in FIG. 5, the microcard sample tray is used without a heated cover. Microcard sample tray 140 may also be used with a heated cover.

It will be apparent to those skilled in the art that various modifications and variations can be made to the structure. Thus, it should be understood that the invention is not limited to the examples discussed in the specification. Rather, the present invention is intended to cover modifications and variations.

What is claimed is:

1. A detection system for a plurality of biological samples, comprising:
   at least one light source for illuminating a plurality of biological samples;
   a light detection device for detecting light received from the plurality of biological samples;
   a lens comprising first and second surfaces formed on the lens, the second surface substantially opposed to the first surface; and
   a heated cover comprising a surface, a lip disposed above the surface and about a perimeter of the cover, and a plurality of openings, the heated cover configured to receive the lens;

wherein, during operation, the first surface is configured to direct light from the light source toward the plurality of biological samples and the second surface is configured to direct the light into each of the plurality of biological samples;

wherein the second surface comprises a matrix of lenses; and wherein the openings of the heated cover are tapered from an upper edge of the opening to a lower edge of the opening.

2. The detection system of claim 1, wherein the heated cover is disposed between the sample block and the lens.

3. The detection system of claim 1, further comprising a thermal cycler configured to cycle a temperature of the samples.

4. The detection system of claim 1, wherein the detection system is configured to perform a nucleic acid amplification on a plurality of samples.

5. The detection system of claim 1, wherein the detection system is configured to perform a polymerase chain reaction on a plurality of samples.

6. The detection system of claim 1, wherein a plurality of focusing lens portions corresponds to a plurality of biological samples.

7. The detection system of claim 1, further comprising a sample block assembly configured to receive a sample well tray.

8. The detection system of claim 1, wherein the first surface comprises a Fresnel lens surface.

9. The detection system of claim 1, further comprising a sample block for receiving the plurality of biological samples.

10. The detection system of claim 9, wherein the sample block comprises a plurality of openings for receiving the plurality of samples.

11. The detection system of claim 1, wherein the lens comprises a non-fluorescing polycarbonate material.

12. The detection system of claim 1, wherein a plurality of focusing lens portions is configured to direct light of an approximately equal intensity into a plurality of biological samples.

13. The detection system of claim 1, wherein one or more of the plurality of focusing lens portions is configured to allow differing light intensity to pass through than at least one other of the plurality of focusing lens portions.

14. The detection system of claim 1, wherein the lens is located on the lip and above the surface.

15. A detection system for a plurality of biological samples, comprising:
    at least one light source for illuminating a plurality of biological samples;
    a light detection device for detecting light received from the plurality of biological samples;
    a lens comprising first and second surfaces formed on the lens, the second surface substantially opposed to the first surface; and
    a heated cover comprising a plurality of openings;
    wherein, during operation, the first surface is configured to direct light from the light source toward the plurality of biological samples and the second surface is configured to direct the light into each of the plurality of biological samples;
    wherein the second surface comprises a matrix of lenses, at least some of the lenses corresponding to respective openings of the plurality of openings; and
    wherein at least one of the openings is tapered from an upper edge of the at least one opening to a lower edge of the at least one opening.

16. The detection system of claim 15, wherein the heated cover further comprises a lip disposed about a perimeter of the heated cover.

17. The detection system of claim 16, wherein the lip is configured to receive the matrix of lenses.

* * * * *